(12) United States Patent
Lakshmi et al.

(10) Patent No.: US 10,973,798 B2
(45) Date of Patent: Apr. 13, 2021

(54) DISPERSION OF FORMONONETIN SOLID LIPID NANOPARTICLES AND PROCESS FOR ITS PREPARATION

(71) Applicant: SRM INSTITUTE OF SCIENCE AND TECHNOLOGY, Chennai (IN)

(72) Inventors: Karunanidhi Santhana Lakshmi, Chennai (IN); Vaithialingam Jagannathan Vishnu Varthan, Chennai (IN)

(73) Assignee: SRM INSTITUTE OF SCIENCE AND TECHNOLOGY, Chennai (IN)

( * ) Notice: Subject to any disclaimer, the term of this patent is extended or adjusted under 35 U.S.C. 154(b) by 0 days.

(21) Appl. No.: 16/231,540

(22) Filed: Dec. 23, 2018

(65) Prior Publication Data

US 2020/0197360 A1    Jun. 25, 2020

(51) Int. Cl.
| | |
|---|---|
| A61K 9/10 | (2006.01) |
| A61K 9/51 | (2006.01) |
| A61K 47/26 | (2006.01) |
| A61P 35/00 | (2006.01) |
| A61P 29/00 | (2006.01) |
| A61K 31/353 | (2006.01) |
| A61K 47/12 | (2006.01) |
| A61K 47/10 | (2017.01) |
| A61P 3/10 | (2006.01) |
| A61P 19/10 | (2006.01) |
| A61K 47/20 | (2006.01) |
| B82Y 5/00 | (2011.01) |

(52) U.S. Cl.
CPC .......... *A61K 31/353* (2013.01); *A61K 9/10* (2013.01); *A61K 9/5123* (2013.01); *A61K 47/10* (2013.01); *A61K 47/12* (2013.01); *A61K 47/20* (2013.01); *A61K 47/26* (2013.01); *A61P 3/10* (2018.01); *A61P 19/10* (2018.01); *A61P 29/00* (2018.01); *A61P 35/00* (2018.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 5,858,410 A | * | 1/1999 | Muller ................. | A61K 9/0019 424/489 |
| 6,153,208 A | * | 11/2000 | McAtee ............... | A61K 8/0208 424/402 |

OTHER PUBLICATIONS

Wang et al. (Nanostructured Lipid Carriers as delivery systems for biochanin A, Drug Deliver 2013, 20:8, 331-337). (Year: 2013).*

(Continued)

*Primary Examiner* — Melissa S Mercier
(74) *Attorney, Agent, or Firm* — The Roy Gross Law Firm, LLC; Roy Gross

(57) ABSTRACT

A dispersion of formononetin solid lipid nanoparticles and process for its preparation, namely having (i) a core system comprising formononetin, a lipid base, and a fluid medium, and (ii) an emulsifier system comprising an emulsifier, and water. The dispersion of formononetin solid lipid nanoparticles of the present disclosure can be used for treating cancer, osteoporosis, diabetes, and inflammation. The dispersion of formononetin solid lipid nanoparticles of the present disclosure are biocompatible, biodegradable, has improved solubility, has enhanced controlled drug release profile and are stable.

9 Claims, 21 Drawing Sheets

(56) References Cited

OTHER PUBLICATIONS

Wang et al. (Nanostructured lipid carriers as a delivery system of biochanin A, Drug Delivery, 2013; 20(8); 311-337 (Year: 2013).*

* cited by examiner

DISPERSION OF FORMONONETIN SOLID LIPID NANOPARTICLES AND PROCESS FOR ITS PREPARATION

FIELD OF THE INVENTION

The present disclosure relates to a dispersion of formononetin solid lipid nanoparticles and a process for its preparation.

Definitions

As used in the present disclosure, the following terms are generally intended to have the meaning as set forth below, except to the extent that the context in which they are used indicates otherwise.

Percentage of entrapment efficiency: The term "Percentage of Entrapment efficiency" refers to the percentage of drug that is successfully entrapped into the micelle or nanoparticle.

Drug Release Kinetics:

Mathematical models describe the drug release behavior from a formulation.

The system in which drug release and concentration exhibit zero dependency was well explained by Zero order equation.

The equation for zero order release is $Q_t = Q_0 + K_0 \, t$
Where $Q_t$ = cumulative amount of drug release at time "t"
$Q_0$ = Initial amount of drug
$K_0$ = Zero order release constant
t = time in hours Whereas, First order rate equation explains the system release which is dependent on concentration. The equation for first order release is $\text{Log } Q_t = \text{Log } Q_0 + Kt/2.303$
Where $Q_0$ = initial amount of drug
$Q_t$ = cumulative amount of drug release at time "t"
K = First order release constant
t = time in hours Likewise, Higuchi equation postulated theory for insoluble drug matrix, proposing that rate of release as square root of time following a fickian diffusion. The equation for Higuchi equation is $Q = K_H t^{1/2}$
Whereas Q = cumulative amount of drug release at time "t"
$K_H$ = Higuchi constant
t = Time in hours Hixon-crowell law explains the release behavior in which change in surface area and diameter of particle is observed. The equation for Hixon-crowell equation is $3\sqrt{Q_0} - 3\sqrt{Qt} = K_{HC} \cdot t$
Whereas Q0 = Initial amount of drug
Qt = Cumulative amount of drug release at time "t"
KHC = Hixson crowell release constant
t = Time in hours In addition to these mathematical models, korsemeyer peppas equation describes the drug release in diffusion controlled release system. This model also explains the fickian behavior of drug release. The equation for Korsemeyer peppas is $F = (M_t/M) = K_m t^n$
Where F = Fraction of drug released at time 't'
Mt = Amount of drug released at time T
M = Total amount of drug in dosage form
Km = Kinetic constant
n = Diffusion or release exponent
t = Time in hours

BACKGROUND OF THE INVENTION

The background information herein below relates to the present disclosure but is not necessarily prior art.

Formononetin is an o-methylated isoflavone. Formononetin possess diverse pharmacological activities such as anti-cancer, anti-osteoporosis, anti-diabetic, and anti-inflammatory. However, due to poor oral bioavailability of formononetin, it fails to attain the pharmacological activity with the desired dose. In addition, the formulations having formononetin are not biocompatible, and are unstable.

Therefore, there is felt a need for a formulation that mitigates the aforestated drawbacks.

OBJECTS OF THE INVENTION

Some of the objects of the present disclosure, which at least one embodiment herein satisfies, are as follows:

It is an object of the present disclosure is to ameliorate one or more problems of the prior art or to at least provide a useful alternative.

An object of the present disclosure is to provide a dispersion of formononetin solid lipid nanoparticles that are stable.

Another object of the present disclosure is to provide a dispersion of formononetin solid lipid nanoparticles that has enhanced controlled release profile.

Still another object of the present disclosure is to provide a dispersion of formononetin solid lipid nanoparticles that are biocompatible and biodegradable.

Yet another object of the present disclosure is to provide a process for the preparation of dispersion of formononetin solid lipid nanoparticles.

Other objects and advantages of the present disclosure will be more apparent from the following description, which is not intended to limit the scope of the present disclosure.

SUMMARY OF THE INVENTION

In an aspect of the present disclosure, a dispersion of formononetin solid lipid nanoparticles is provided. The dispersion comprises (i) a core system comprising formononetin, a lipid base, and a fluid medium, and (ii) an emulsifier system comprising an emulsifier, and water.

In accordance with an embodiment of the present disclosure, a dispersion of formononetin solid lipid nanoparticles comprises (a) a core system comprising formononetin in an amount in the range of 15 wt % to 25 wt % of the total weight of the dispersion, a lipid base in an amount in the range of 15 wt % to 35 wt % of the total weight of the dispersion, and a fluid medium in an amount in the range of 5 wt % to 15 wt % of the total weight of the dispersion, and (b) an emulsifier system comprising an emulsifier in an amount in the range of 0.1 wt % to 0.6 wt % of the total weight of the dispersion, and water in an amount in the range of 40 wt % to 60 wt % of the total weight of the dispersion.

The particle size of the formononetin solid lipid nanoparticles is in the range of 200 nm to 350 nm. The zeta potential of the formononetin solid lipid nanoparticles is in the range of −25.00 mv to −45.00 mv. The percentage of entrapment efficiency of the formononetin solid lipid nanoparticles is in the range of 40% to 75%.

The release of formononetin from the solid lipid nanoparticles is in the range of 70% to 90%.

In another aspect of the present disclosure, there is provided a process for preparing the dispersion of formononetin solid lipid nanoparticles. The process comprises dissolution of predetermined amounts of formononetin and lipid base in a fluid medium at a temperature in the range of 50° C. to 70° C. to obtain a solution. The predetermined amount of at least one emulsifier is separately mixed with water to obtain an aqueous emulsion. The so obtained solution is injected into the aqueous emulsion under continuous stirring to obtain the dispersion of formononetin solid lipid nanoparticles, wherein the particle size of solid lipid nanoparticles is in the range of 200 nm to 350 nm.

BRIEF DESCRIPTION OF THE DRAWINGS

The present disclosure will now be described with the help of the accompanying drawing, in which.

DETAILED DESCRIPTION OF THE INVENTION

Figure 1:
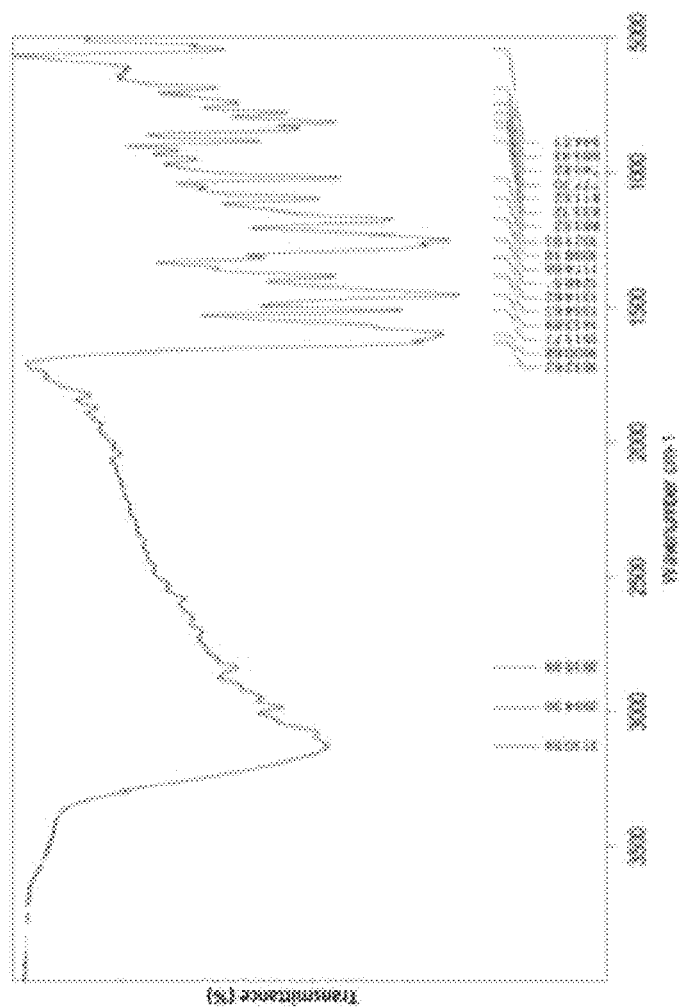
FIG. 1 depicts an FT-IR spectroscopy of formononetin (raw drug)

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

As used herein, the term "and/or" includes any and all combinations of one or more of the associated listed elements.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

Formononetin has diverse pharmacological activities such as anti-cancer, anti-osteoporosis, anti-diabetic, and anti-inflammatory. However, due to poor oral bioavailability of formononetin, it fails to attain the pharmacological activity. Also, the formulations having formononetin are not biocompatible, and are unstable.

Therefore, the present disclosure envisages a formulation that mitigates the aforestated drawbacks.

In an aspect of the present disclosure, a dispersion of formononetin solid lipid nanoparticles is provided. The dispersion comprises a core system and an emulsifier system. The core system comprises formononetin, a lipid base, and a fluid medium. The emulsifier system comprises an emulsifier, and water.

The amount of formononetin can be in the range of 15 wt % to 25 wt % of the total weight of the dispersion. In an embodiment, the amount of formononetin is 20 wt % of the total weight of the dispersion In accordance with an embodiment of the present disclosure, the lipid base is stearic acid. The amount of lipid base can be in the range of 15 wt % to 35 wt % of the total weight of the dispersion. In an embodiment, the amount of lipid base is 25 wt % of the total weight of the dispersion.

The fluid medium can be selected from the group consisting of ethanol, methanol, propanol, butanol and dimethyl sulphoxide. In one embodiment, the fluid medium is methanol. The amount of fluid medium can be in the range of 5 wt % to 15 wt % of the total weight of the dispersion. In one embodiment, the amount of fluid medium is 10 wt % of the total weight of the dispersion. The fluid medium is used to solubilize both formononetin and the lipid base as formononetin is not completely soluble in the lipid base.

The emulsifier is selected from the group consisting of polyoxyethylene (20) sorbitan monooleate, and sorbitan monolaurate. The amount of the emulsifier can be in the range of 0.1 wt % to 0.6 wt % of the total weight of the dispersion. In an embodiment, the amount of the emulsifier is 0.4 wt % of the total weight of the dispersion. The emulsifiers are used to obtain a colloidal dispersion of formononetin loaded solid lipid nanoparticles. The amount of water can be used in the range of 40 wt % to 60 wt % of the total weight of the solid lipid nanoparticles that is used along with the emulsifier in the emulsifier system.

In accordance with the present disclosure, the particle size of the formononetin solid lipid nanoparticles in the dispersion is in the range of 200 nm to 350 nm. The formononetin loaded solid lipid nanoparticles, having particle size in the range of 200 nm to 350 nm, with a lipid base can ultimately be absorbed into the cells, thereby enabling good biocompatibility with enhanced bioavailability.

The zeta potential of the formononetin solid lipid nanoparticles in the dispersion is in the range of −25.00 mv to −45.00 mv. For the assessment of the physical stability of the solid lipid nanoparticles, zeta potential, which is the electrical potential of the particle is an important parameter. Due to ionization of the surface groups, the surface of the particles in dispersion develops charge which depends on both the surface chemistry of the particle and the media around these particles. Around the particle, the surface charge generates a potential which might be highest near the surface and decays with distance into the medium. Zeta potential is measured by determining the velocity of the particle in an electrical field. The zeta potential of the solid lipid nanoparticles, in the range of −25.00 to −45.00 mV, which are very high zeta potential values, lead to more stable nanoparticles and overcome the tendency of aggregation due to van der waals forces.

The percentage of entrapment efficiency of the formononetin solid lipid nanoparticles of the dispersion of the present disclosure is in the range of 40% to 75%. The entrapment efficiency of the solid lipid nanoparticles of the present disclosure results in enhanced formononetin loading on the solid lipid nanoparticles, since the lipid content of the solid lipid nanoparticles of the present disclosure is high i.e., in the range of 20 wt % to 35 wt % of the total weight of the solid lipid nanoparticles.

The release of formononetin from the solid lipid nanoparticles of the dispersion of the present disclosure is in the range of 70% to 90%, which means the solid lipid nanoparticles of the present disclosure has improved controlled drug release profile.

In another aspect of the present disclosure, there is provided a process for preparing the dispersion of formononetin solid lipid nanoparticles. The process comprises dissolution of predetermined amounts of formononetin and lipid base in a fluid medium at a temperature in the range of 50° C. to 70° C. to obtain a solution. The predetermined amount of at least one emulsifier is separately mixed with water to obtain an aqueous emulsion. The so obtained solution is injected into the aqueous emulsion under continuous stirring to obtain the dispersion of formononetin solid lipid nanoparticles, wherein the particle size of solid lipid nanoparticles is in the range of 200 nm to 350 nm.

Overall, the dispersion of formononetin solid lipid nanoparticles of the present disclosure are biocompatible, biodegradable, have better controlled drug release profile, have better solubility, and are stable.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAIL

Experiment 1: Formulation of Formononetin Solid Lipid Nanoparticles (SLNs) in the Form of Dispersion in Accordance with the Present Disclosure Four formulations of formononetin SLNs in the form of dispersion were prepared by the solvent injection method. The various formulations of formononetin SLNs in the form of dispersion are given in the Table-1.

TABLE 1

Formulations of formononetin SLNs in the form of dispersion

|  | F1 | F2 | F3 | F4 |
| --- | --- | --- | --- | --- |
| Internal phase | | | | |
| Formononetin (mg) | 20 mg | 20 mg | 20 mg | 20 mg |
| Stearic acid (mg) | 20 mg | 30 mg | 20 mg | 30 mg |
| Ethanol (ml) | 10 ml | 10 ml | 10 ml | 10 ml |
| External Phase | | | | |
| Tween 80 (ml) | 0.3 ml | 0.3 ml | 0.3 ml | 0.3 ml |
| Span 20 (ml) | 0.1 ml | 0.1 ml | 0.2 ml | 0.2 ml |
| Water (ml) | 50 ml | 50 ml | 50 ml | 50 ml |

General Process for the Preparation of the Dispersion of Formononetin Solid Lipid Nanoparticles:

Formononetin and stearic acid were dissolved in a predetermined amount of fluid medium, with heating at melting temperature of 60° C. to obtain a solution. The resulting solution was rapidly injected into 10 ml of an aqueous emulsion containing a predetermined amounts of polyoxyethylene (20) sorbitan monooleate (tween 80), and sorbitan monolaurate (span 20) which was continuously stirred at 400 rpm for 30 minutes on a magnetic stirrer to obtain the dispersion of formononetin SLNs. Finally, the dispersion of formononetin SLNs was stored at 0° C.-4° C. for long term storage. The dispersion of formononetin SLNs can be stored for 12 to 24 months.

Experiment 2: Characterization of Formononetin Solid Lipid Nanoparticles

Figure 2:
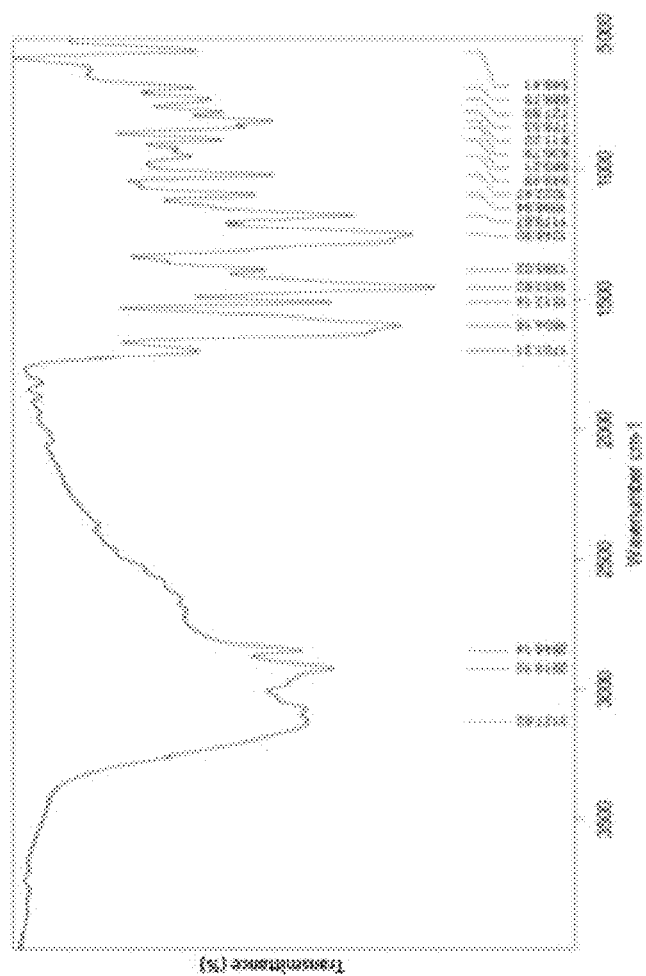
FIG. 2 depicts an FT-IR spectroscopy of formononetin and stearic acid.
Figure 3:
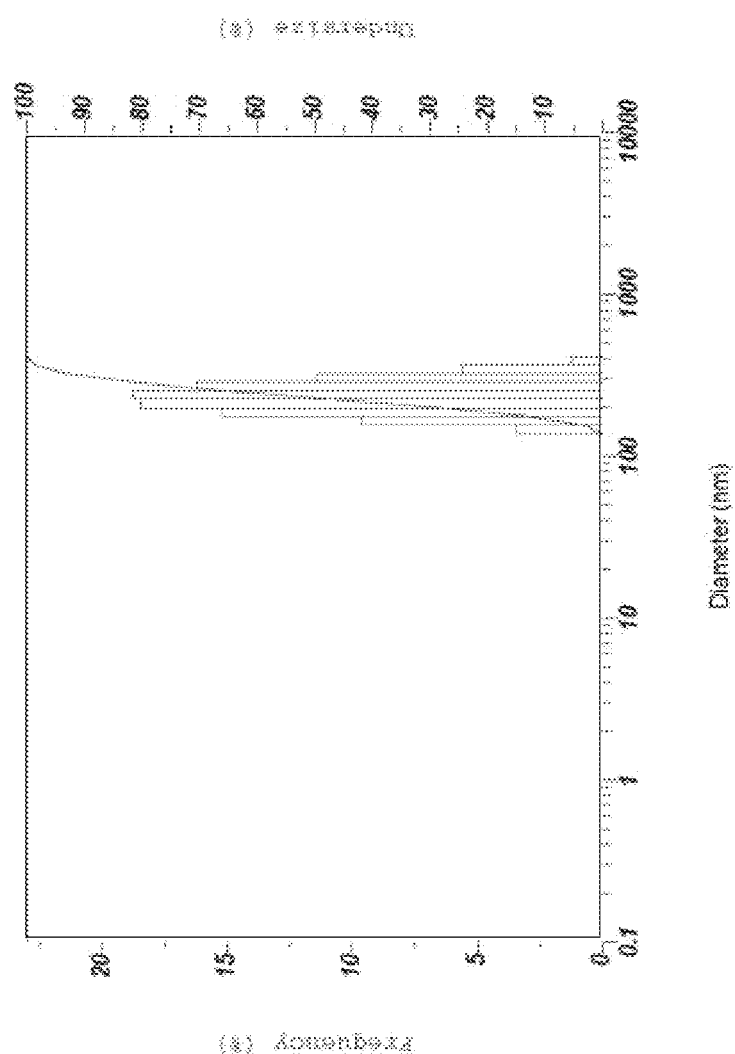
FIG. 3 depicts a graphical representation of particles size of formononetin solid lipid nanoparticles in the dispersion of the present disclosure (F1)
Figure 4:
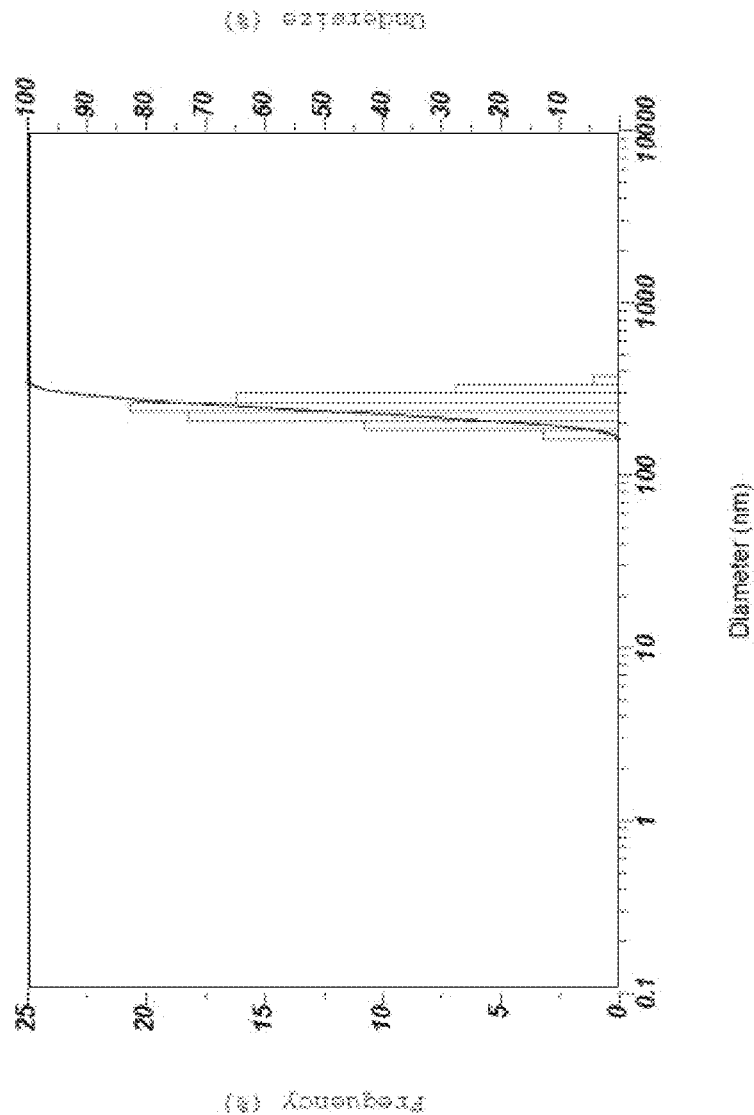
FIG. 4 depicts a graphical representation of particles size of formononetin solid lipid nanoparticles in the dispersion of the present disclosure (F2)
Figure 5:
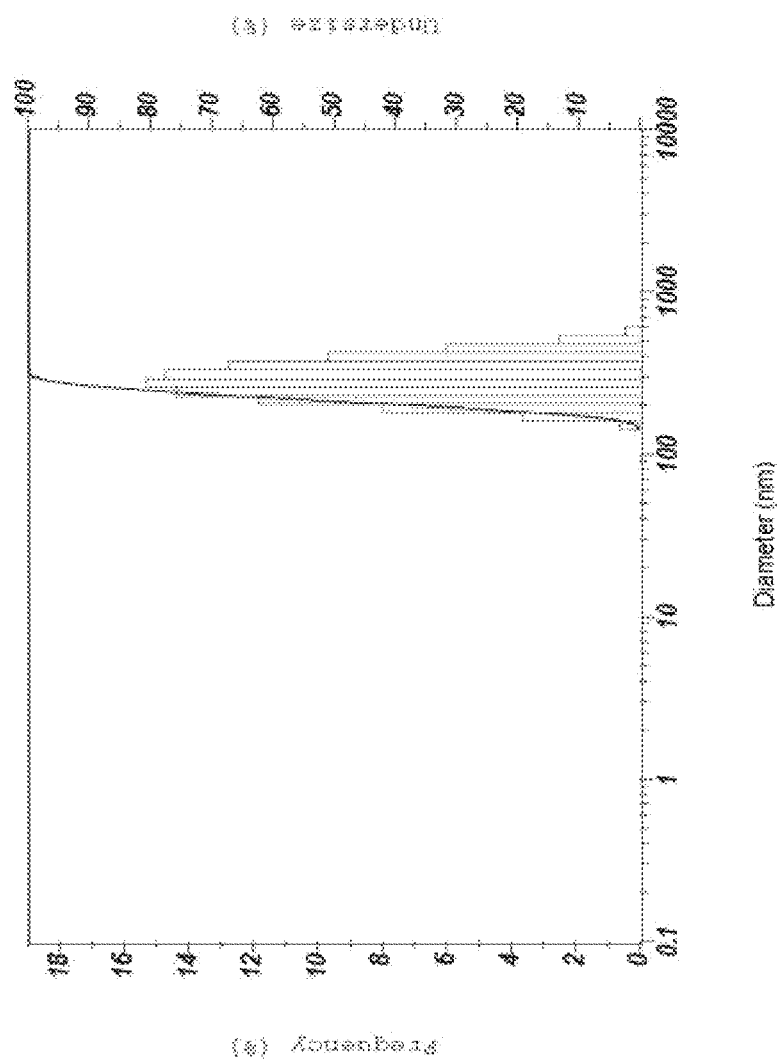
FIG. 5 depicts a graphical representation of particles size of formononetin solid lipid nanoparticles in the dispersion of the present disclosure (F3)
Figure 6:
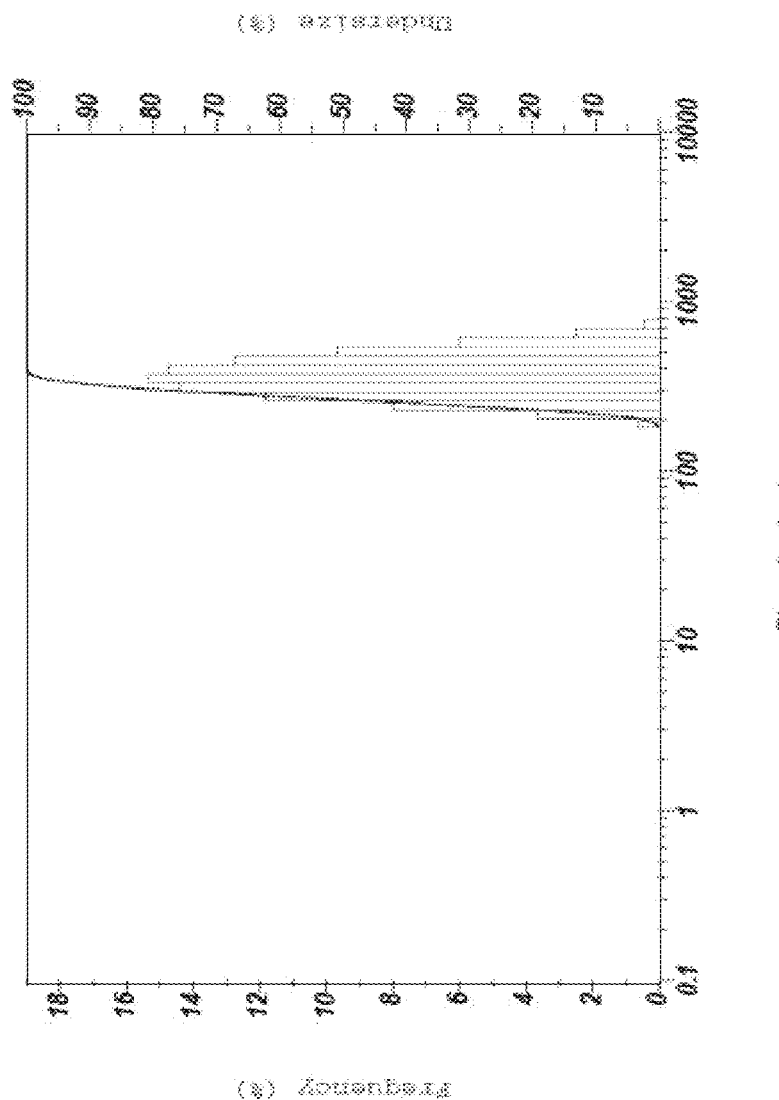
FIG. 6 depicts a graphical representation of particles size of formononetin solid lipid nanoparticles in the dispersion of the present disclosure (F4)
Figure 7:
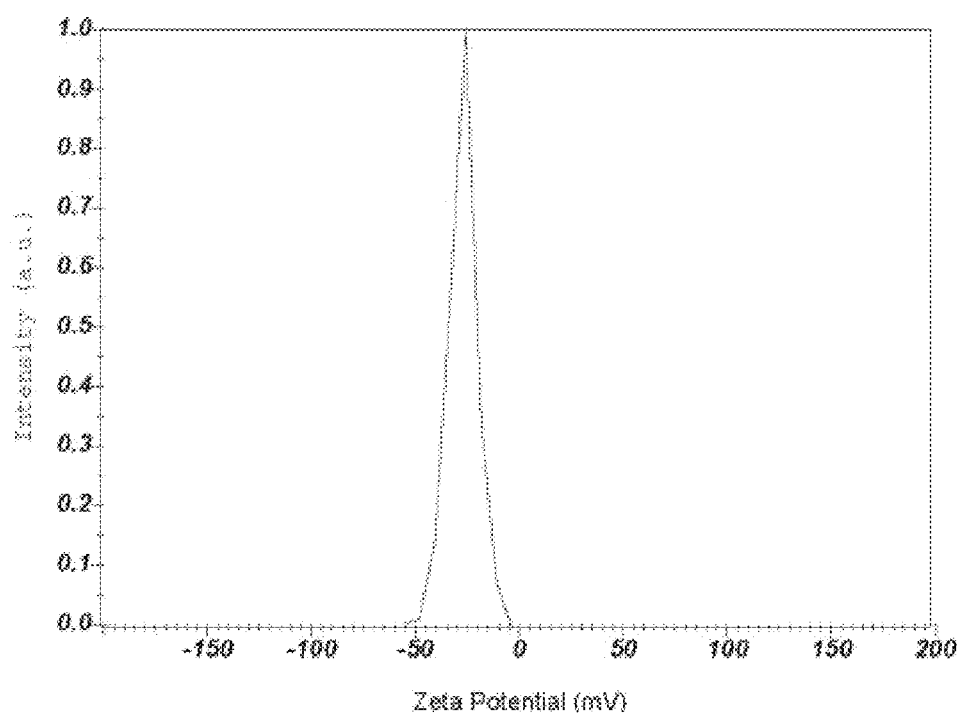
FIG. 7 depicts a graphical representation of Zeta potential of formononetin solid lipid nanoparticles in the dispersion of the present disclosure (F1)
Figure 8:
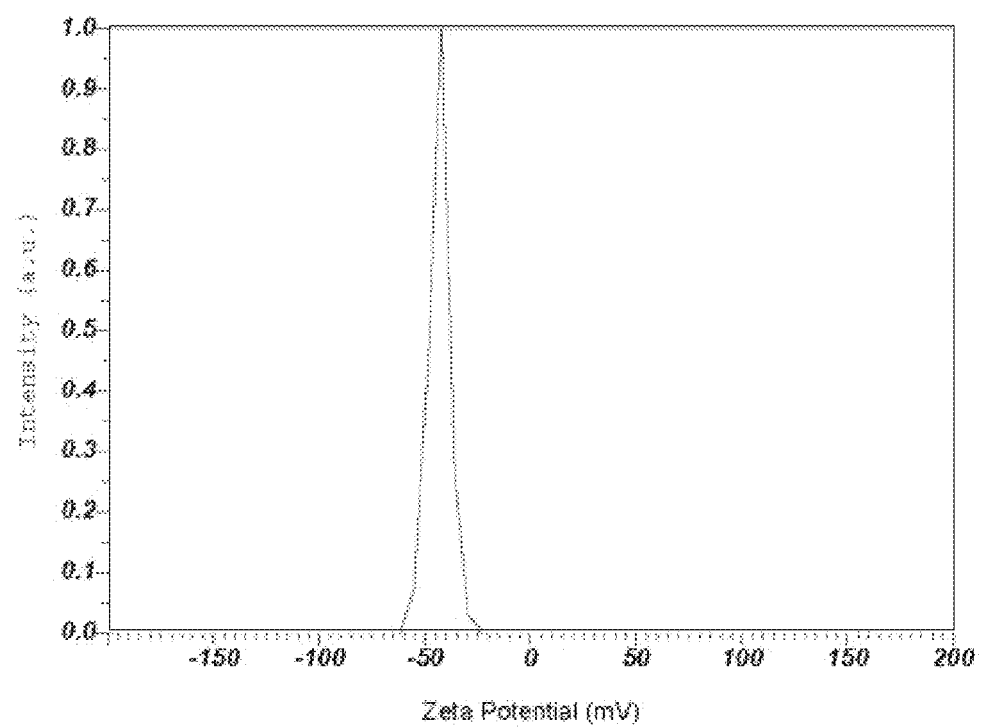
FIG. 8 depicts a graphical representation of Zeta potential of formononetin solid lipid nanoparticles in the dispersion of the present disclosure (F2)
Figure 9:
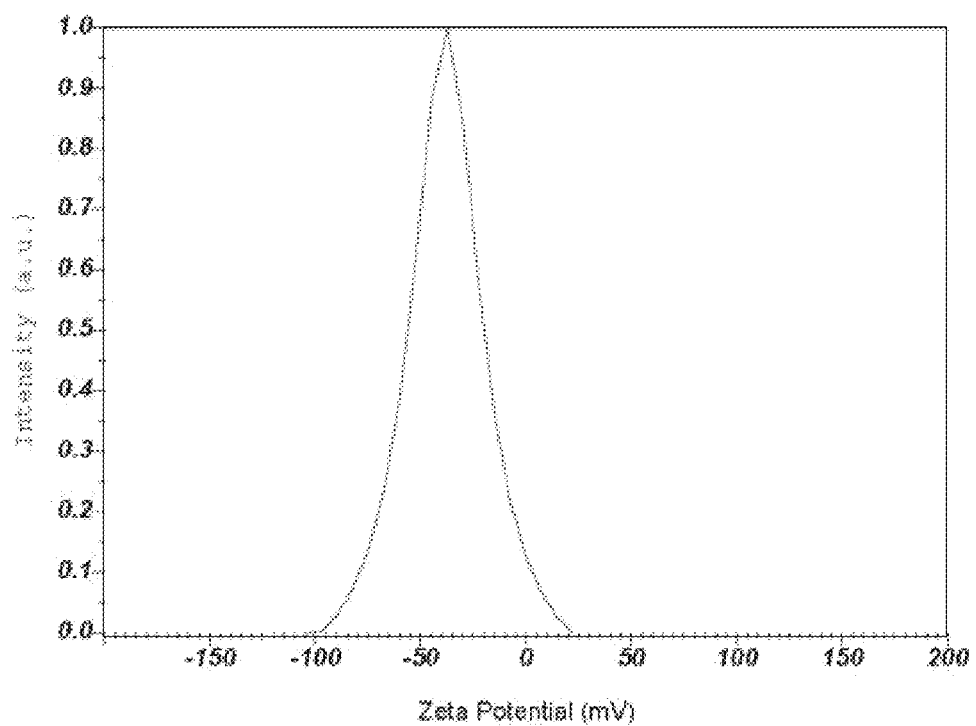
FIG. 9 depicts a graphical representation of Zeta potential of formononetin solid lipid nanoparticles in the dispersion of the present disclosure (F3)
Figure 10:
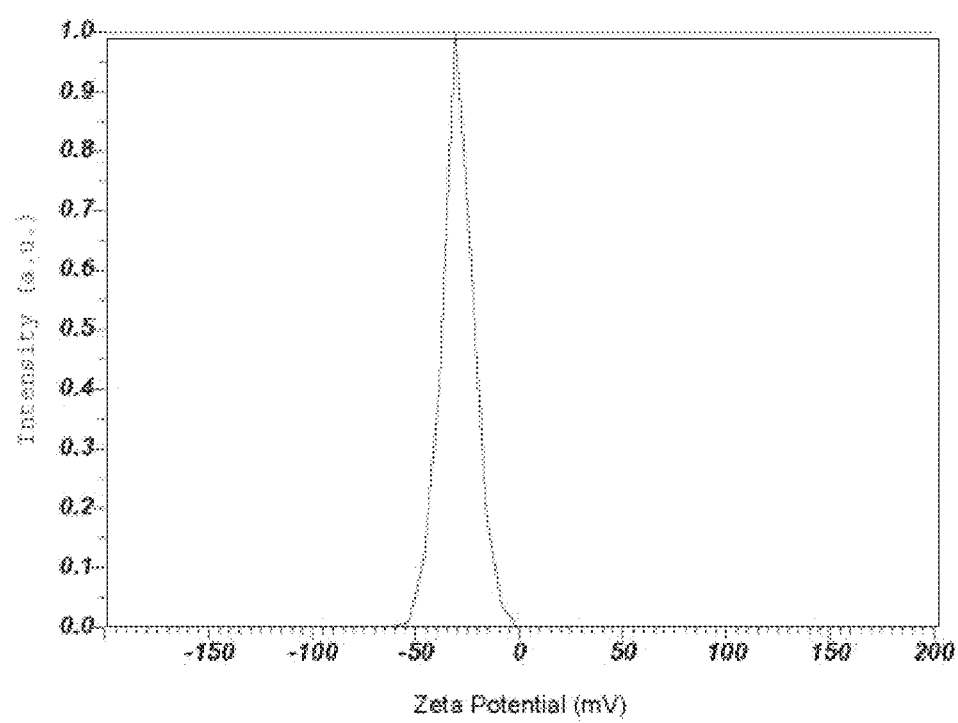
FIG. 10 depicts a graphical representation of Zeta potential of formononetin solid lipid nanoparticles in the dispersion of the present disclosure (F4)

1. Fourier Transform-Infra Red (FT-IR) Spectroscopy of Formononetin Solid Lipid Nanoparticles The formononetin and excipients mixture compatibility studies were carried out by using FT-IR. FT-IR spectra of formononetin solid lipid nanoparticles were measured using Perkin-Elmer FTIR spectroscopy. 5 mg of the sample was mixed with 100 mg of potassium bromide and compressed into the pellet using a hydraulic press. The FT-IR scanning range of 4000-400 $cm^{-1}$ was obtained with a resolution of 2 $cm^{-1}$. The results are shown in Table-2, FIG. 1 and FIG. 2.

TABLE 2

Results for Fourier transform—infra red spectroscopy of formononetin solid lipid nanoparticles

| S. NO | Compound | Vibration | Types of Vibration | Possible Group |
|---|---|---|---|---|
| 1. | Formononetin | 3130 | Stretching | O—H |
| | | 2984, 2835 | Stretching | C—H |
| | | 1632, 1600, 1511 | Stretching | Conjugation of C=C |
| | | 1453, 1174 | Cyclic ester Stretching | Cyclic ester C=O |
| | | 883, 777, 740 | Aromatic carbon Stretching | Aromatic Carbon |
| | | 3127 | Stretching | C—H |
| | | 2919, 2848 | Stretching | C—H |
| 2. | Formononetin + Stearic acid | 1701 | Conjugation stretching | Conjugation of C=O |
| | | 1604 | conjugation stretching | Conjugation of C=C |
| | | 1512, 1453, 1385 | Aromatic Ring stretching | C=C Aromatic ring |
| | | 1248, 1179, 1098, 1022 | Stretching | C=O |
| | | 949, 885, 836, 811 | Aromatic Carbon stretching | Aromatic Carbon |

It is evident from table 2 that as compared to Formononetin (raw drug), the combination of Formononetin and steric acid, in aromatic carbon stretching has formed one more additional peak and a small shift has occurred towards higher wavelength. In C=O, stretching, 2 more additional peaks were produced and the slight shift towards lower wavelength. Conjugation C=C showed only one peak when compared to Formononetin (raw drug). All these factors confirm the conjugation of Formononetin with stearic acid and there is no interaction between the Formononetin and the steric acid. These results showed that there is no interaction between the Formononetin and the excipients, which confirm that formononetin molecule remains intact. Therefore, formononetin and stearic acid are compatible with each other.

2. Particle Size Analysis of the Formononetin Solid Lipid Nanoparticles in the Dispersion of the Present Disclosure The mean particle size of formononetin SLNs was determined using Horiba SZ-100 version 2.00 (Horiba scientific, Tirupathi). Briefly, 1 milligram of the dispersion of formononetin SLNs was suspended in 3 ml of double distilled water and sonicated for 30 seconds. The method was done in a triplicate manner.

The results are tabulated in the table-3 and in FIGS. 3, 4, 5 and 6 for particle size.

TABLE 3

Results of particle size analysis of formononetin solid lipid nanoparticle formulations in the form of dispersion

| S. No | Nano formulations | Particle size (nm) |
|---|---|---|
| 1. | F1 | 225.7 ± 1.332*** |
| 2. | F2 | 260.4 ± 1.300*** |
| 3. | F3 | 292.9 ± 0.845*** |
| 4. | F4 | 329.9 ± 1.852*** |

Values are expressed as mean ± SEM, n = 3, *$P < 0.001$ vs. formulations, $P < 0.01$ vs. formulations, *$P < 0.05$ vs. Formulations; one way ANOVA followed by Bonferroni post comparison test all pairs of the column.

From table 3, it is evident that the particle size of formononetin solid lipid nanoparticles is found to be in the range of 225.7 nm to 329.9 nm. It is reported that increase in the lipid content results in larger particle size. The similar results are obtained for the dispersion F2 and F4 in which quantity of stearic acid is more when compared to F1 and F3. Particle size for all the dispersions are found to be significant <0.0001.

The dispersion of formononetin loaded solid lipid nanoparticles of the present disclosure, having particle size in the range of 225.7 nm to 329.9 nm, with a lipid base can ultimately be absorbed into the cells, thereby enabling good biocompatibility with enhanced bioavailability.

3. Determining Zeta Potential of the Formononetin Solid Lipid Nanoparticles in the Dispersion of the Present Disclosure The stability of the nanoparticles is based upon the zeta potential values of the SLNs formulations. The Zeta potential for all the four dispersions of formononetin SLNs was in the range of −25.55 mv to −42.01 mv which shows formononetin in SLNs form has good stability. The results are tabulated in the table-4 and in FIGS. 7, 8, 9 and 10 for zeta potential.

TABLE 4

Results of determining zeta potential of formononetin solid lipid nanoparticle formulations in the form of dispersion

| S. No | Nano formulations | Zeta potential (mV) |
|---|---|---|
| 1. | F1 | −25.55 ± 1.414*** |
| 2. | F2 | −42.01 ± 0.927*** |
| 3. | F3 | −37.20 ± 0.977* |
| 4. | F4 | −31.11 ± 0.861* |

Values are expressed as mean ± SEM, n = 3, *$P < 0.001$ vs. formulations, $P < 0.01$ vs. formulations, *$P < 0.05$ vs. Formulations; one way ANOVA followed by Bonferroni post comparison test all pairs of the column.

For the assessment of the physical stability of the solid lipid nanoparticles, zeta potential, which is the electrical potential of the particle is an important parameter. By determining the velocity of the solid lipid nanoparticles in an electrical field, zeta potential can be measured.

From table 4, it is evident that all the four dispersions of formononetin solid lipid nanoparticles showed the zeta potential in the range of −25 to −42 mV. High zeta potential values lead to more stable nanoparticles and overcome the tendency of aggregation due to van der waals forces. Therefore, these high zeta potential values of the solid lipid nanoparticles of the present disclosure leads to more stable nanoparticles and overcome the tendency of aggregation due to van der waals forces.

4. Determining Drug Entrapment Efficiency and Drug Loading Capacity of Formononetin Solid Lipid Nanoparticles in the Dispersion of the Present Disclosure The entrapment efficiency which corresponds to the percentage of formononetin encapsulated within and absorbed onto the nanoparticles was determined by measuring the concentration of free formononetin in the dispersing medium by adding 1 ml of dispersion of formononetin SLNs was centrifuged at 6000 rpm for 45 min. The supernatant was separated and filtered through filter paper 0.2 μm filter. The filtrate was diluted with ethanol and measured spectrophotometrically.

The entrapment efficiency was calculated using the following equation and the results are tabulated in table-5.

$$\text{Percentage of Entrapment Efficiency} = \frac{W \text{ Initial Drug} - W \text{ Free Drug}}{W \text{ Initial}} \times 100$$

W Initial Drug is the mass of the initial drug used, i.e., amount of formononetin used initially for the preparation of SLNs formulation.

W Free drug is the mass of the free drug (unentrapped) detected, i.e., amount of free formononetin in the filtrate.

TABLE 5

Results of determining drug entrapment efficiency and drug loading capacity of formononetin solid lipid nanoparticle formulations in the form of dispersion

| S. No | Nano formulations | % Entrapment efficiency |
|---|---|---|
| 1. | F1 | 60.57 ± 0.465*** |
| 2. | F2 | 66.47 ± 0.428*** |
| 3. | F3 | 49.75 ± 0.684*** |
| 4. | F4 | 40.54 ± 0.395*** |

Values are expressed as mean ± SEM, n = 3, *$P < 0.001$ vs. formulations, $P < 0.01$ vs. ANOVA formulations, *$P < 0.05$ vs. Formulations; one way followed by Bonferroni post comparison test all pairs of the column.

From table 5, it is evident that all the dispersions of formononetin SLNs showed the percentage of entrapment efficiency in the range of 40-75%. The percentage of entrapment efficiency is found to be more in the dispersion F2. It is reported that the dispersion with low lipid concentration will have lower entrapment efficiency but the dispersion F2 with high lipid content (30 mg of stearic acid) showed the maximum entrapment efficiency (66.47%) but with the same concentration of lipid with little increase in the span 20 showed lower percentage of entrapment F4 (40.54%). This is due to the change in the HLB value because HLB values also play an important role in making the affinity of the drug to get entrapped in the matrix.

These percentage of entrapment efficiency of the solid lipid nanoparticles of the present disclosure results in enhanced formononetin loading on the solid lipid nanoparticles, since the lipid content of the solid lipid nanoparticles of the present disclosure is high i.e., in the range of 20 wt % to 35 wt % of the total weight of the dispersion.

Figure 11:
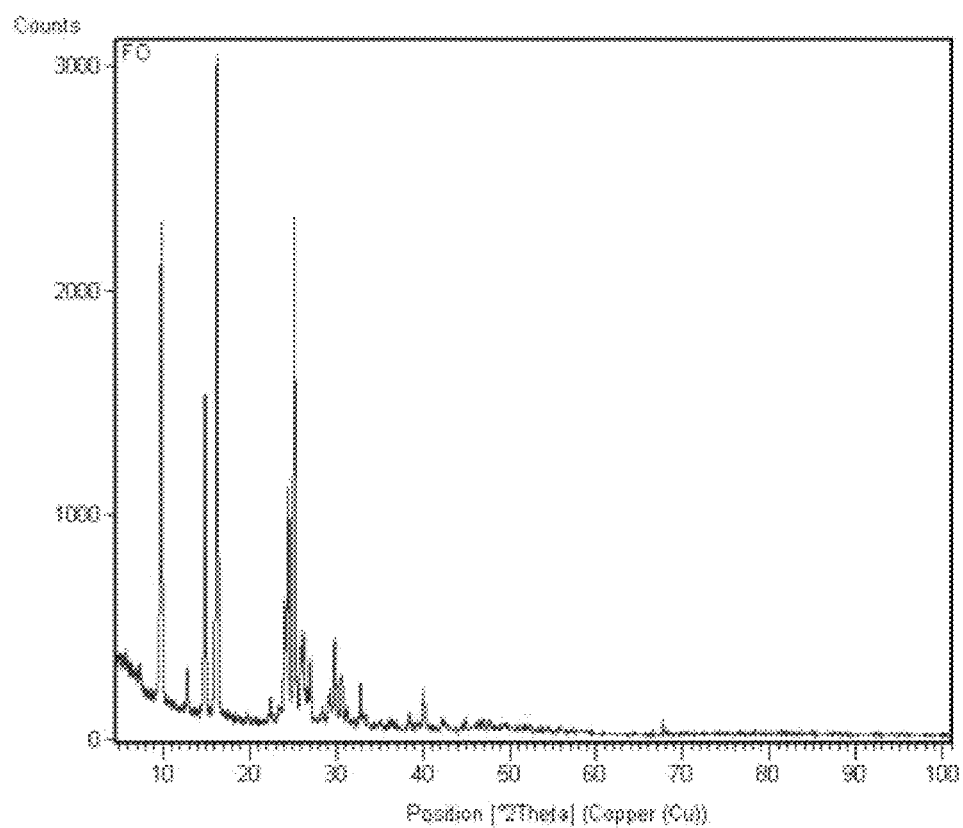
FIG. 11 depicts an X-ray powder diffractogram of formononetin (raw drug)
Figure 12:
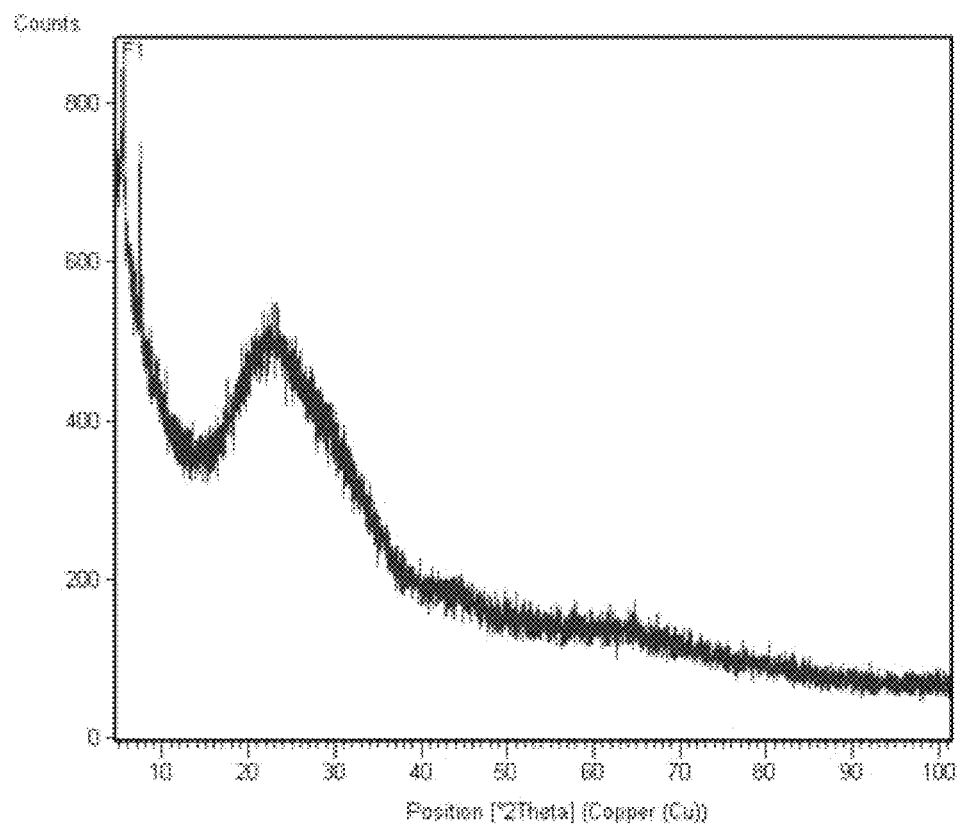
FIG. 12 depicts an X-ray powder diffractogram of formononetin solid lipid nanoparticles in the dispersion of the present disclosure (F1)
Figure 13:
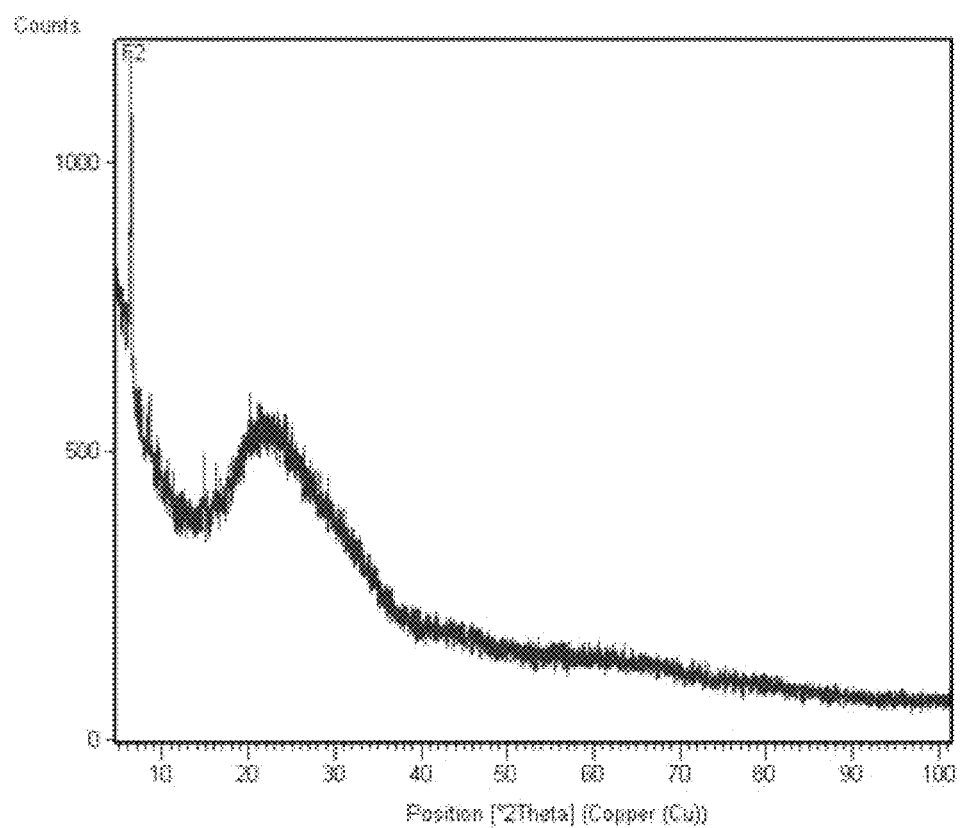
FIG. 13 depicts an X-ray powder diffractogram of formononetin solid lipid nanoparticles in the dispersion of the present disclosure (F2)
Figure 14:
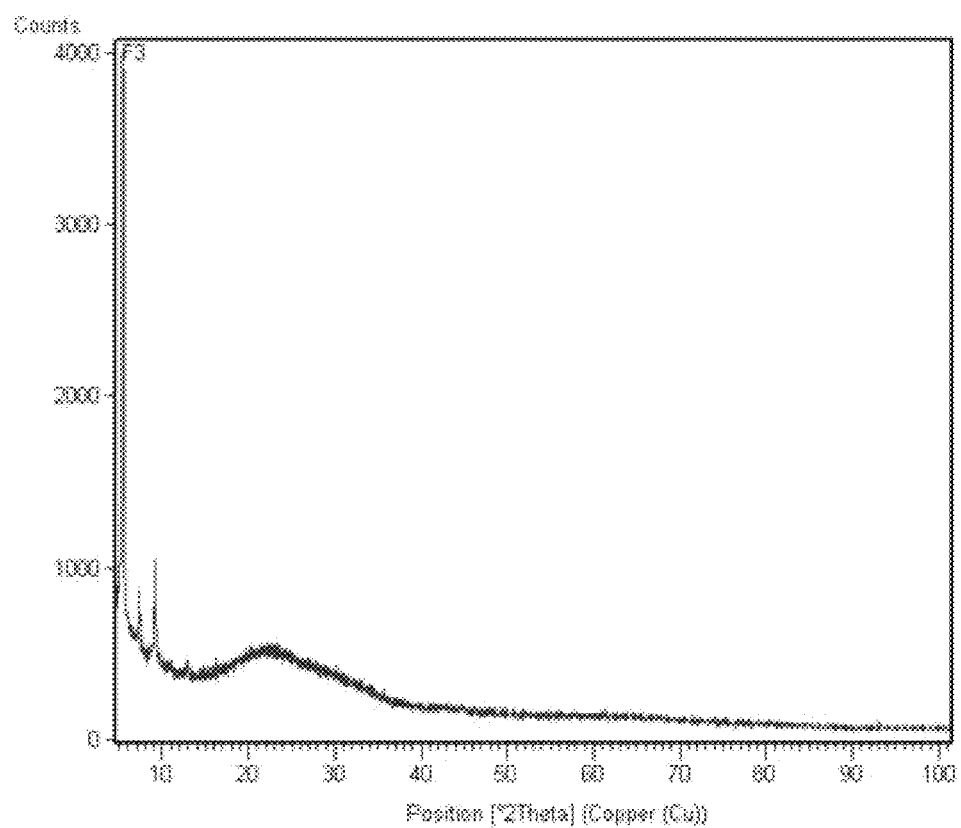
FIG. 14 depicts an X-ray powder diffractogram of formononetin solid lipid nanoparticles in the dispersion of the present disclosure (F3)
Figure 15:
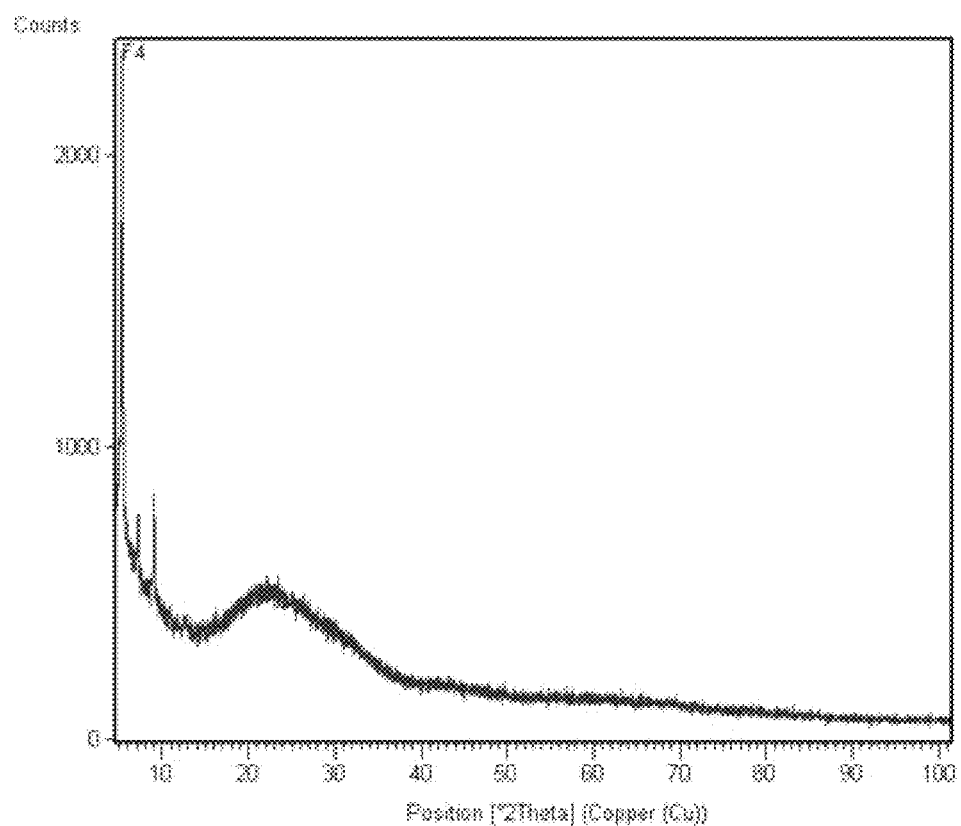
FIG. 15 depicts an X-ray powder diffractogram of formononetin solid lipid nanoparticles in the dispersion of the present disclosure (F4)
Figure 16:
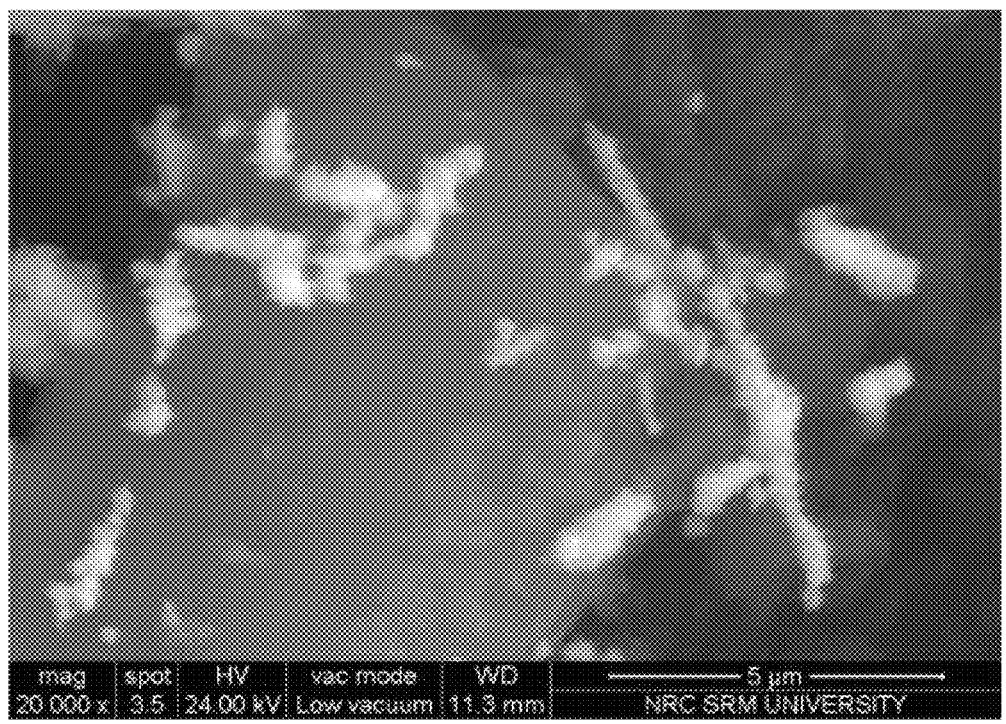
FIG. 16 depicts a Scanning electron microscopy of formononetin (raw drug)
Figure 17:
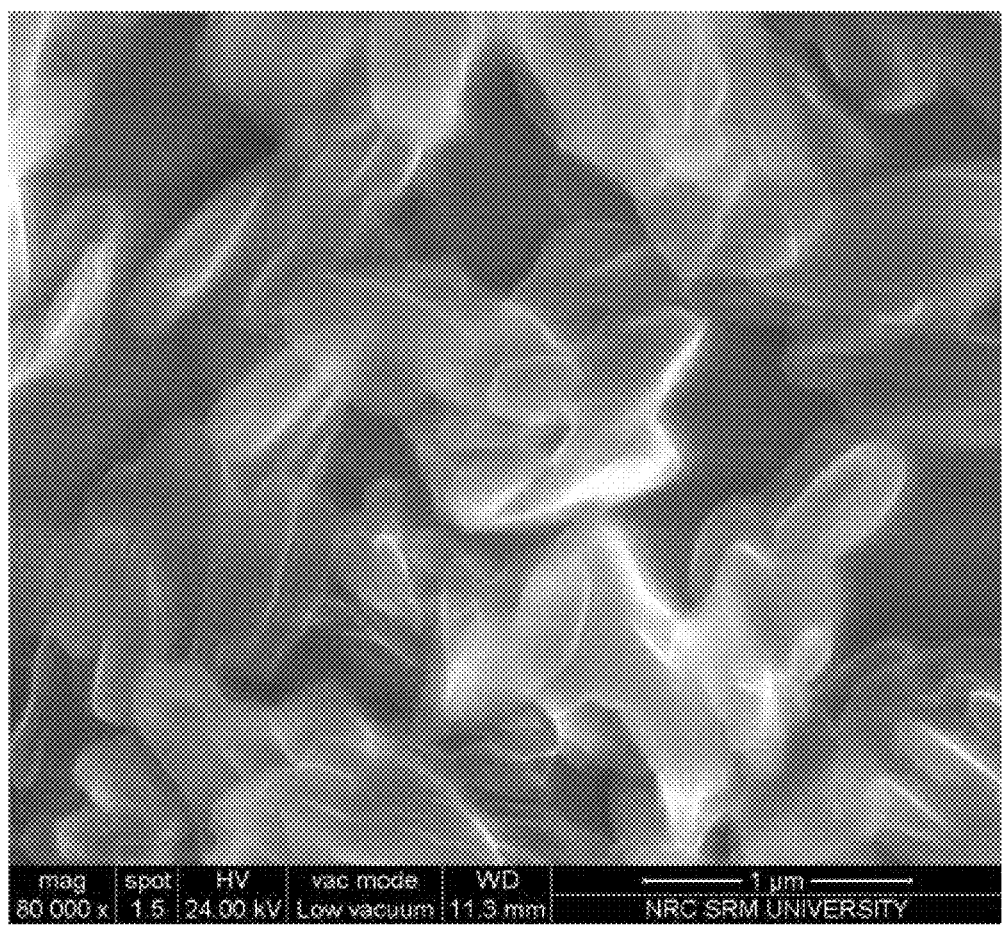
FIG. 17 depicts a Scanning electron microscopy of formononetin solid lipid nanoparticles in the dispersion of the present disclosure (F1)
Figure 18:
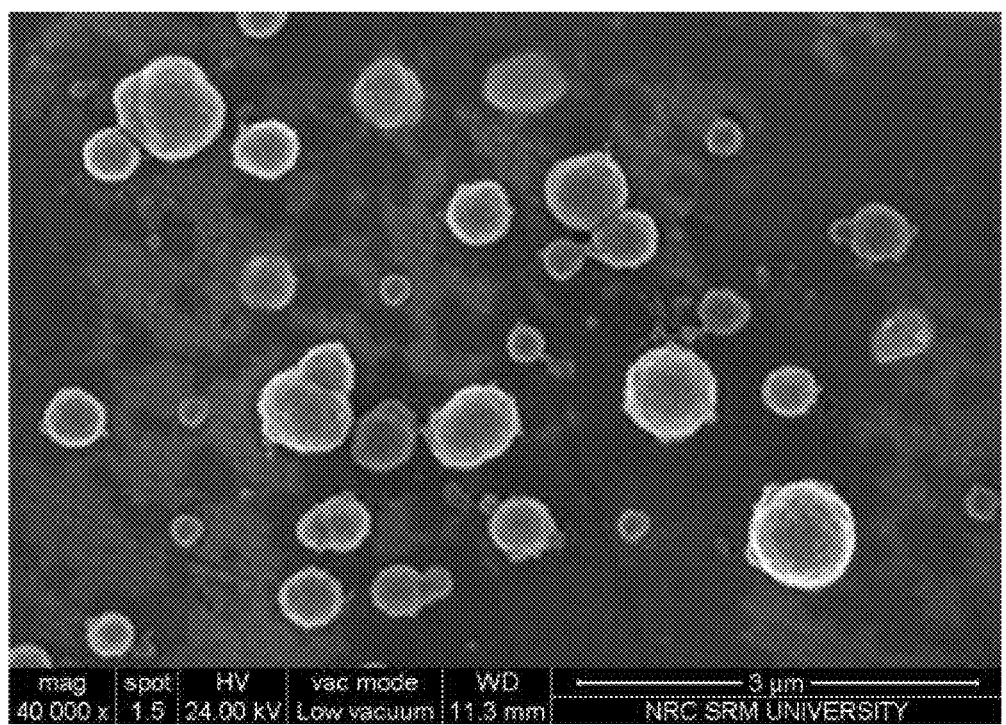
FIG. 18 depicts a Scanning electron microscopy of formononetin solid lipid nanoparticles in the dispersion of the present disclosure (F2)
Figure 19:
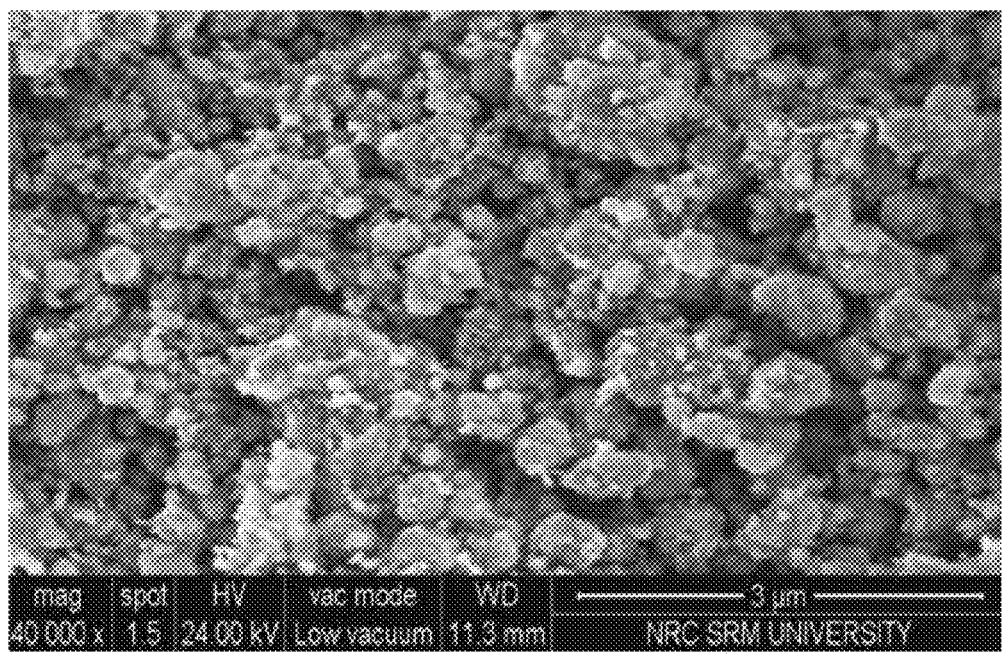
FIG. 19 depicts a Scanning electron microscopy of formononetin solid lipid nanoparticles in the dispersion of the present disclosure (F3)
Figure 20:
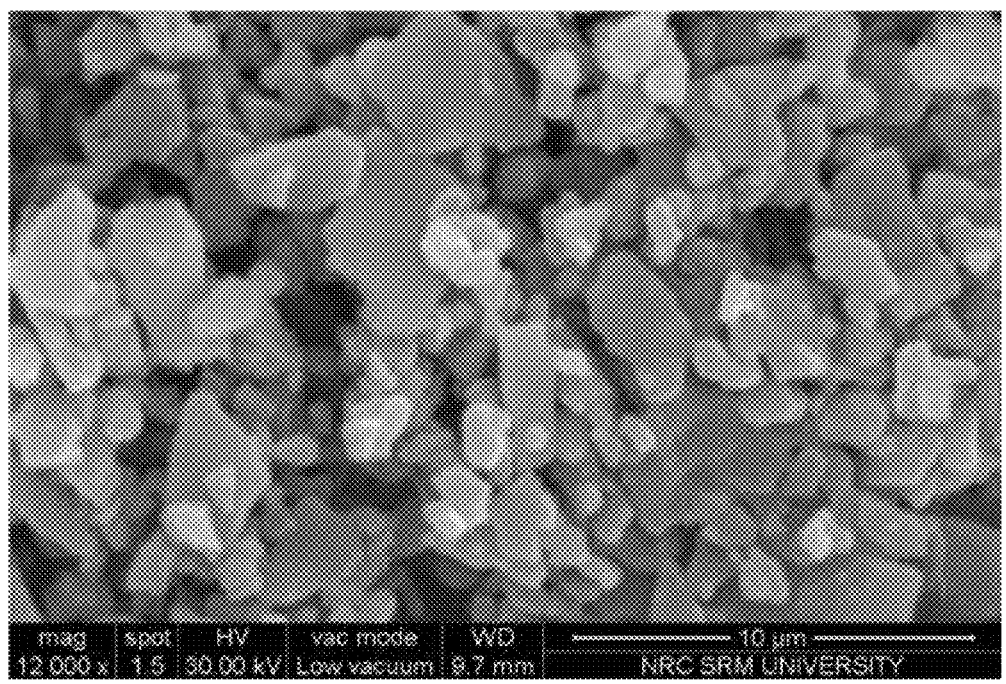
FIG. 20 depicts a Scanning electron microscopy of formononetin solid lipid nanoparticles in the dispersion of the present disclosure (F4)

5. Biodegradability Analysis of Formononetin Solid Lipid Nanoparticles in the Dispersion of the Present Disclosure
X-Ray Diffraction Study X-ray diffraction study was performed to study the nature of the dispersions of the present disclosure. The results are shown in FIG. 11 for the pure drug (Formononetin) and FIGS. 12, 13, 14 and 15 for the dispersions F1, F2, F3 and F4, respectively.

From the X-ray diffraction studies, it is evident that the pure drug Formononetin has crystalline character which was seen from the XRD as a sharp intense peak, whereas XRD of formononetin loaded SLNs does not have the sharp intense peaks which evidenced that the crystallinity has been converted into amorphous character. This provides enhanced solubility of the formononetin.

6. Scanning Electron Microscopy of Formononetin Solid Lipid Nanoparticles in the Dispersion of the Present Disclosure SEM analysis was done for the solid lipid nanoparticles in order to study the shape and surface of the dispersions. Briefly, 0.5 mg/ml of formononetin SLNs was suspended in water and sonicated for 30 seconds. One drop of nanoparticle suspension was placed and visualized under the microscope. The results are shown in FIGS. 16, 17, 18, 19 and 20.

From FIGS. 16-20, it is evident that the formononetin solid lipid nanoparticles have the spherical shape with smooth surfaces.

7. In-Vitro Drug Release Profile of the Formononetin Solid Lipid Nanoparticles in the Dispersion of the Present Disclosure In-vitro drug release of SLNs of the present disclosure was performed by the dialysis bag diffusion technique. Solid lipid nanoparticle preparation was loaded in a dialysis membrane (12-14 K DA pore size 2.4 nm) and immersed in a receptor compartment containing 900 ml of phosphate buffer pH 7.4 stirred at 100 rpm at a temperature between 37±0.5° C. Two ml of the aliquots were withdrawn in a regular time interval (0, 30, 60, 120, 240, 360, 480, 600, 720, 1440 min) and replenishment of the receptor compartment with the same volume of fresh medium. The percentage cumulative drug release vs. time was noted. The results of the in-vitro drug release profile are shown in FIG. 21.

Figure 21:
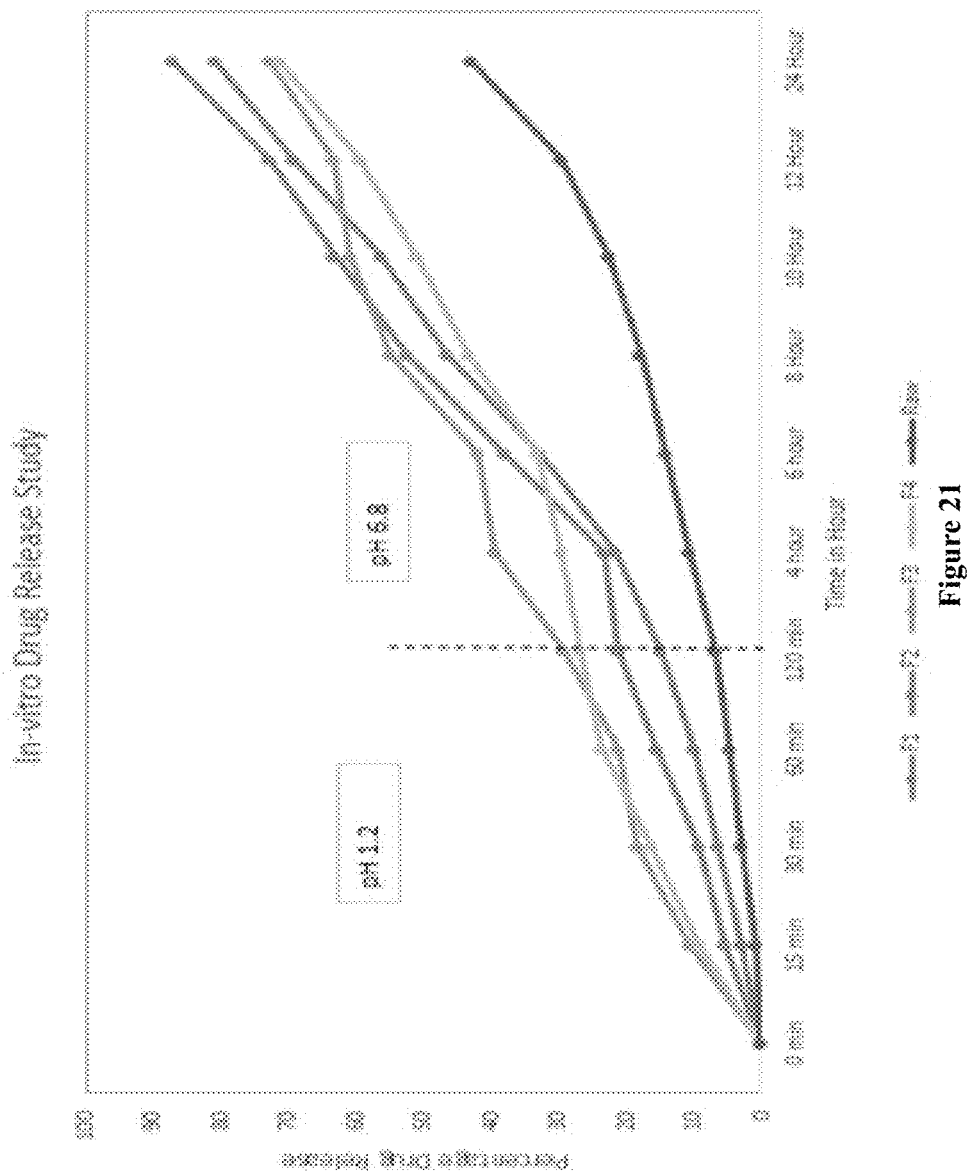
FIG. 21 depicts a graphical representation of in-vitro drug release for formononetin (raw drug) and for the dispersions of formononetin solid lipid nanoparticles (F1, F2, F3, and F4) of the present disclosure.

From FIG. 21, it is evident that the drug release for all the dispersions of the formononetin SLNs are in the range of 71.7% to 87.64%, while the raw drug formononetin showed 43.31% of release.

Further, in-vitro drug release kinetics for formononetin SLNs of the dispersions of the present disclosure were determined and the results are provided in tables 6.

TABLE 6

In vitro release order Kinetics of the formononetin solid lipid nanoparticles

| Release order of Kinetics | Formulations R2 | | | |
|---|---|---|---|---|
| | F1 | F2 | F3 | F4 |
| Zero Order | 0.8833 | 0.8906 | 0.7804 | 0.8544 |
| First Order | 0.9744 | 0.9621 | 0.8939 | 0.946 |
| Higuchi Equation | 0.9579 | 0.9582 | 0.9584 | 0.9629 |
| Hixon crowell | 0.9568 | 0.944 | 0.8589 | 0.9212 |
| Korsmeyer peppas | 0.9786 | 0.985 | 0.9829 | 0.9555 |
| N Value | 0.618 | 0.739 | 0.416 | 0.408 |

From table 6, it is evident that the solid lipid nanoparticles release the drug in the controlled or sustained manner which can result in the prolonged half-life and retarded enzymatic attack in the systemic circulation. F1 and F2 follows non-fickian type of drug release mechanism, whereas F3 and F4 follows fickian type of drug release since the 'n' value lies in the range of $0.45 < n < 0.89$ for the formononetin solid lipid nanoparticles of the present disclosure and 'n' value less than 0.45 for the latter formulations. In fickian type of drug release, the polymer relaxation time is approximately equal to solvent diffusion time, whereas in non-fickian type of drug release, the polymer relaxation time is greater than the solvent diffusion time.

Overall, from the above study, it is evident that the dispersion of formononetin solid lipid nanoparticles of the present disclosure are biocompatible, biodegradable, have better controlled drug release profile, have better solubility, and are stable.

TECHNICAL ADVANCEMENTS

The present disclosure described herein above has several technical advantages including, but not limited to, the realization of solid lipid nanoparticles that:
are biocompatible;
are biodegradable
have improved solubility;
have enhanced controlled drug release profile; and
are stable.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A dispersion of formononetin solid lipid nanoparticles comprising:
   i) a core system (an internal phase) comprising: formononetin;
   a lipid base, wherein the lipid base is stearic acid; and
   a fluid medium, wherein the fluid medium is selected from the group consisting of ethanol, methanol, and dimethyl sulphoxide; and
   ii) an emulsifier system (an external phase) comprising:
   an emulsifier, wherein the emulsifier is selected from the group consisting of polyoxyethylene (20) sorbitan monooleate, and sorbitan monolaurate; and
   water;
   wherein a ratio of the formononetin to the lipid base is in the range of 1:1 to 1:1.5; and
   wherein the release of formononetin from the solid lipid nanoparticles is in the range of 70% to 90% in a time period of 24 hours through a dialysis membrane (12-14 kDa pore size 2.4 nm) immersed in a receptor compartment containing phosphate buffer pH 7.4 and stirred at 100 rpm at a temperature between 37±0.5° C.

2. A dispersion of formononetin solid lipid nanoparticles comprising:
   a) a core system (an internal phase) comprising:
   formononetin in an amount in the range of 15 wt. % to 25 wt. % of the total weight of the dispersion;
   a lipid base in an amount in the range of 15 wt. % to 35 wt. % of the total weight of the dispersion; wherein the lipid base is stearic acid; and
   a fluid medium in an amount in the range of 5 wt. % to 15 wt. % of the total weight of the dispersion, wherein the fluid medium is selected from the group consisting of ethanol methanol and dimethyl sulphoxide; and
   b) an emulsifier system (an external phase) comprising:
   an emulsifier in an amount in the range of 0.1 wt. % to 0.6 wt. % of the total weight of the dispersion; wherein the emulsifier is selected from the group consisting of polyoxyethylene (20) sorbitan monooleate and sorbitan monolaurate; and
   water in an amount in the range of 40 wt. % to 60 wt. % of the total weight of the dispersion;
   wherein a ratio of the formononetin to the lipid base is in the range of 1:1 to 1:1.5; and
   wherein the release of formononetin from the solid lipid nanoparticles is in the range of 70% to 90% in a time period of 24 hours through a dialysis membrane (12-14 kDa pore size 2.4 nm) immersed in a receptor compartment containing phosphate buffer pH 7.4 and stirred at 100 rpm at a temperature between 37±0.5° C.

3. The dispersion as claimed in claim 1, wherein the particle size of solid lipid nanoparticles is in the range of 200 nm to 350 nm.

4. A dispersion of formononetin solid lipid nanoparticles comprising:
   i) a core system (an internal phase) comprising:
   formononetin;
   a lipid base, wherein the lipid base is stearic acid; and a fluid medium, wherein the fluid medium is selected from the group consisting of ethanol methanol and dimethyl sulphoxide; and ii) an emulsifier system (an external phase) comprising:
an emulsifier, wherein the emulsifier is selected from the group consisting of polyoxyethylene (20) sorbitan monooleate and sorbitan monolaurate; and
water,
wherein the zeta potential of the solid lipid nanoparticles is in the range of −25.00 mv to −45.00 mv.

5. The dispersion as claimed in claim 1, wherein the percentage of entrapment efficiency of the solid lipid nanoparticles is in the range of 40% to 75%.

6. The dispersion as claimed in claim 1 is used for the treatment of cancer, osteoporosis, diabetes, and inflammation.

7. The dispersion as claimed in claim 2, wherein the particle size of solid lipid nanoparticles is in the range of 200 nm to 350 nm.

8. The dispersion as claimed in claim 2, wherein the zeta potential of the solid lipid nanoparticles is in the range of −25.00 mv to −45.00 mv.

9. The dispersion as claimed in claim 2, wherein the percentage of entrapment efficiency of the solid lipid nanoparticles is in the range of 40% to 75%.

\* \* \* \* \*